(12) United States Patent
Li et al.

(10) Patent No.: US 8,703,787 B2
(45) Date of Patent: Apr. 22, 2014

(54) METHODS OF USING ALK INHIBITORS

(75) Inventors: Nanxin Li, San Diego, CA (US);
Jennifer Leslie Harris, San Diego, CA (US); Peter McNamara, San Diego, CA (US); Fangxian Sun, Melrose, MA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 13/981,046

(22) PCT Filed: Feb. 2, 2012

(86) PCT No.: PCT/US2012/023669
§ 371 (c)(1),
(2), (4) Date: Jul. 22, 2013

(87) PCT Pub. No.: WO2012/106540
PCT Pub. Date: Aug. 9, 2012

(65) Prior Publication Data
US 2013/0296357 A1    Nov. 7, 2013

Related U.S. Application Data

(60) Provisional application No. 61/438,878, filed on Feb. 2, 2011.

(51) Int. Cl.
*A61K 31/505* (2006.01)
*C07D 401/14* (2006.01)

(52) U.S. Cl.
CPC .................................. *C07D 401/14* (2013.01)
USPC ........................................................ 514/275

(58) Field of Classification Search
CPC ...................................................... C07D 401/14
USPC ........................................................ 514/275
See application file for complete search history.

(56) References Cited

FOREIGN PATENT DOCUMENTS

WO    WO2008073687    6/2008

OTHER PUBLICATIONS

Li, et al., "Evaluation of EML4-ALK fusion proteins in non-small cell lung cancer using small molecule inhibitors", Neoplasia, Jan. 2011, pp. 1-11, vol. 13, No. 1.
Zhang et al., "Crizotinib-Resistant Mutants of EML4-ALK Identified Through an Accelerated Mutagenesis Screen", Chemical Biology and Drug Design, Dec. 1, 2011, pp. 999-1005, vol. 78, No. 6.
Katayama et al., "Therapeutic strategies to overcome crizotinib resistance in non-small cell lung cancers harboring the fusion oncogene EML4-ALK", Proceedings of the National Academy of Sciences of the United States of America, May 2011, pp. 1-6, vol. 108, No. 18.

*Primary Examiner* — Raymond Henley, III
(74) *Attorney, Agent, or Firm* — Emily Tongco Wu; Genomics Institute of the Novartis Research Foundation

(57) ABSTRACT

The invention provides methods for using compounds of Formula (I) for treating an EML4-ALK+ mediated condition such as EML4-ALK+ non-small cell lung cancer, and optionally resistant to crizotinib; wherein $R^1$, $R^2$, $R^3$, $R^4$, $R^5$ and $R^6$ are as defined above.

9 Claims, 3 Drawing Sheets

METHODS OF USING ALK INHIBITORS

CROSS-REFERENCE TO RELATED APPLICATIONS

This application is a 371 U.S. national phase application of international application number PCT/US2012/023669, which application claims priority to U.S. provisional patent application No. 61/438,878 filed 2 Feb. 2011, the disclosure of which is incorporated herein by reference in its entirety and for all purposes.

TECHNICAL FIELD

The present invention relates to the use of ALK inhibitors as pharmaceuticals.

BACKGROUND ART

Lung cancer remains the leading cause of cancer deaths in western countries. (Jemal et al., *CA Cancer J. Clin.* 56, 106-130 (2006)). Patients with non-small cell lung cancer (NSCLC), which accounts for ~80% of lung cancer cases, are often diagnosed at advanced stages of the disease. Given that conventional chemotherapeutic regimens only marginally improve the outcome of such individuals, their median survival time is less than one year after diagnosis (Schiller et al., *N. Engl. J. Med.* 346, 92-98 (2002)). Thus, there is a continuing need for new therapeutic treatments for patients with lung cancer. A c-MET/ALK kinase inhibitor crizotinib has demonstrated significant activity in patients with EML4-ALK in clinical studies. However relapse (or acquired resistance) has also been reported. Therefore there is still an unmet need for patients harboring the EML4-ALK fusion.

DISCLOSURE OF THE INVENTION

The present invention provides compounds and pharmaceutical compositions for treating an EML4-ALK$^+$ mediated condition such as EML4-ALK$^+$ non-small cell lung cancer (NSCLC).

In one aspect, the invention provides a method for treating an EML4-ALK$^+$ mediated condition, for example, EML4-ALK$^+$ non-small cell lung cancer, and optionally resistant to crizotinib, comprising administering to a cell or subject a compound of Formula I

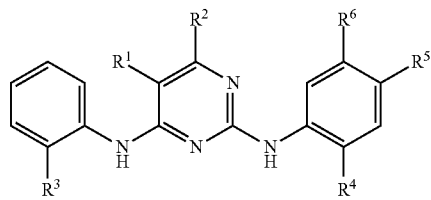

(I)

or a pharmaceutically acceptable salt thereof,
wherein $R^1$ is halo;
$R^2$ is H; or
wherein $R^1$ and $R^2$ together with the carbon atoms to which they are attached form a 5-6 membered heteroaryl comprising 1-2 heteroatoms selected from N, O and S;
$R^3$ is $SO_2R^7$ wherein $R^7$ is $C_{1-6}$ alkyl;
$R^4$ is $C_{1-6}$ alkoxy;
$R^5$ is piperidinyl optionally substituted with $C_{1-6}$ alkyl;
$R^6$ is $C_{1-6}$ alkyl; or
$R^5$ and $R^6$ together with the carbon atoms to which they are attached form a 5-6 membered heterocyclic ring comprising having 1-2 heteroatoms selected from N, O and S.

In one embodiment, $R^1$ in Formula I is chloro. In another embodiment, $R^4$ is isopropoxy. In yet another embodiment, $R^5$ and $R^6$ together with the carbon atoms to which they are attached form $—CH_2—NR^8—C(O)—$, wherein $R^8$ is hydrogen or piperidinyl, optionally substituted with $C_{1-6}$ alkyl.

In another embodiment, the compound is selected from the group:

| Compound | |
|---|---|
| 1 | 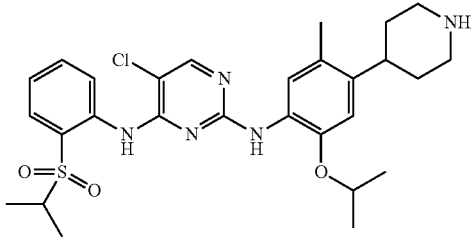 [SMILES: Cc1cc(Nc2ncc(Cl)c(Nc3ccccc3S(=O)(=O)C(C)C)n2)c(OC(C)C)cc1C1CCNCC1]<br>5-chloro-N2-(2-isopropoxy-5-methyl-4-(piperidin-4-yl)phenyl)-N4-[2-(propane-2-sulfonyl)-phenyl]-pyrimidine-2,4-diamine; |
| 2 | 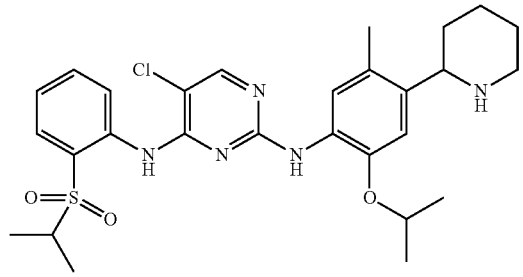 [SMILES: Cc1cc(Nc2ncc(Cl)c(Nc3ccccc3S(=O)(=O)C(C)C)n2)c(OC(C)C)cc1C1CCCCN1]<br>5-chloro-N2-(2-isopropoxy-5-methyl-4-(piperidin-2-yl)phenyl)-N4-(2-(isopropylsulfonyl)phenyl)pyrimidine-2,4-diamine; |
| 3 | 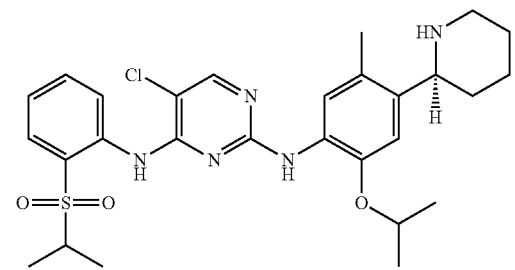 [SMILES: Cc1cc(Nc2ncc(Cl)c(Nc3ccccc3S(=O)(=O)C(C)C)n2)c(OC(C)C)cc1[C@@H]1CCCCN1]<br>(S)-5-chloro-N2-(2-isopropoxy-5-methyl-4-(piperidin-2-yl)phenyl)-N4-(2-(isopropylsulfonyl)phenyl)pyrimidine-2,4-diamine; |

| Compound | |
|---|---|
| 4 | 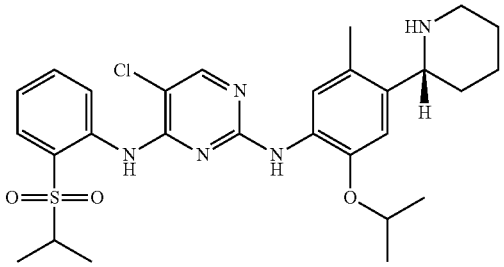 [SMILES: Cc1cc(Nc2ncc(Cl)c(Nc3ccccc3S(=O)(=O)C(C)C)n2)c(OC(C)C)cc1[C@H]1CCCCN1]<br>(R)-5-chloro-N2-(2-isopropoxy-5-methyl-4-(piperidin-2-yl)phenyl)-N4-(2-(isopropylsulfonyl)phenyl)pyrimidine-2,4-diamine; |
| 5 | 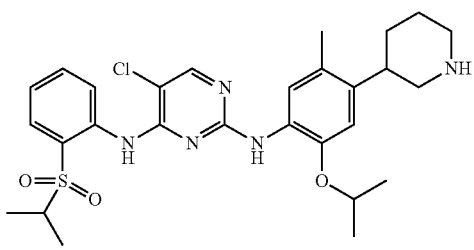 [SMILES: Cc1cc(Nc2ncc(Cl)c(Nc3ccccc3S(=O)(=O)C(C)C)n2)c(OC(C)C)cc1C1CCCNC1]<br>5-chloro-N2-(2-isopropoxy-5-methyl-4-(piperidin-3-yl)phenyl)-N4-(2-(isopropylsulfonyl)phenyl)pyrimidine-2,4-diamine; and |
| 6 | 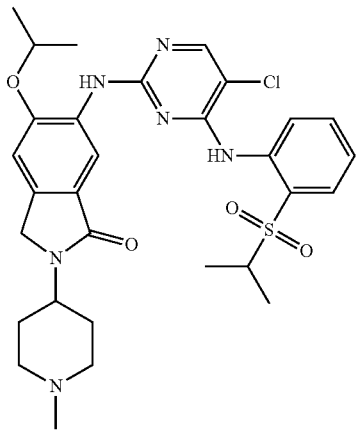 [SMILES: CC(C)Oc1cc2c(cc1Nc1ncc(Cl)c(Nc3ccccc3S(=O)(=O)C(C)C)n1)C(=O)N(C1CCN(C)CC1)C2]<br>6-{5-Chloro-4-[2-(propane-2-sulfonyl)-phenylamino]-pyrimidin-2-ylamino}-5-isopropoxy-2-(1-methyl-piperidin-4-yl)-2,3-dihydro-isoindol-1-one; | or a pharmaceutically acceptable salt thereof.

In particular embodiments, the compound is 5-chloro-N2-(2-isopropoxy-5-methyl-4-(piperidin-4-yl)phenyl)-N4-[2-(propane-2-sulfonyl)-phenyl]-pyrimidine-2,4-diamine or 6-{5-Chloro-4-[2-(propane-2-sulfonyl)-phenylamino]-pyrimidin-2-ylamino}-5-isopropoxy-2-(1-methyl-piperidin-4-yl)-2,3-dihydro-isoindol-1-one.

In another aspect, the invention provides a pharmaceutical composition comprising a compound of Formula I, or any one of compounds 1 to 6, for use in the treatment of an EML4-ALK+ mediated condition, for example EML4-ALK+ non-small cell lung cancer.

In yet another aspect, the invention provides the use of a compound of Formula I, or any one of compounds 1 to 6, for the manufacture of a medicament for the treatment of an EML4-ALK+ mediated condition, for example EML4-ALK+ non-small cell lung cancer.

In another embodiment, the invention pertains to a Compound of Formula I, or any one of compounds 1 to 6, for use in the treatment of an EML4-ALK+ mediated condition, for example EML4-ALK+ non-small cell lung cancer.

In any of the above methods and uses, the compounds of Formula I may be administered to cell or a mammalian subject, particularly a human or animal subject.

MODES OF CARRYING OUT THE INVENTION

Genetic abnormalities on ALK gene locus have been reported to be associated with several cancers. The echinoderm microtubule-associated protein-like 4 (EML4)-ALK fusion due to the chromosome rearrangement was reported in a subset of patients with non-small cell lung cancer (NSCLC). (Soda et al., Nature 448, 561-566 (2007)). Amplification, copy number gain and point mutations of ALK gene have been reported in a subset of neuroblastoma. The compounds of Formula I can be used to treat cancer patients who carry ALK fusion genes due to chromosome rearrangements such as NSCLC patients with EML4-ALK, who carry amplification, copy number gain or point mutations of ALK gene such as neuroblastoma patients, or other patients with tumors characterized by genetic abnormalities in ALK gene or higher expression of ALK than the normal tissue.

In one aspect, the invention provides a method for treating an EML4-ALK+ mediated condition, for example EML4-ALK+ non-small cell lung cancer, and optionally resistant to crizotinib, comprising administering to a cell or subject a compound of Formula I

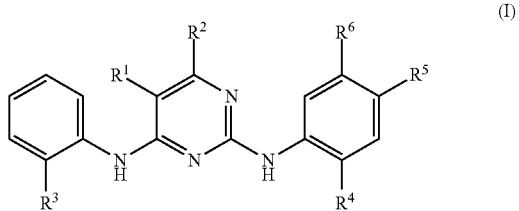

or a pharmaceutically acceptable salt thereof,
wherein $R^1$ is halo;
$R^2$ is H; or
wherein $R^1$ and $R^2$ together with the carbon atoms to which they are attached form a 5-6 membered heteroaryl comprising 1-2 heteroatoms selected from N, O and S;
$R^3$ is $SO_2R^7$ wherein $R^7$ is $C_{1-6}$ alkyl;
$R^4$ is $C_{1-6}$ alkoxy;
$R^5$ is piperidinyl optionally substituted with $C_{1-6}$ alkyl;
$R^6$ is $C_{1-6}$ alkyl; or
$R^5$ and $R^6$ together with the carbon atoms to which they are attached form a 5-6 membered heterocyclic ring comprising having 1-2 heteroatoms selected from N, O and S.

Figure 1:
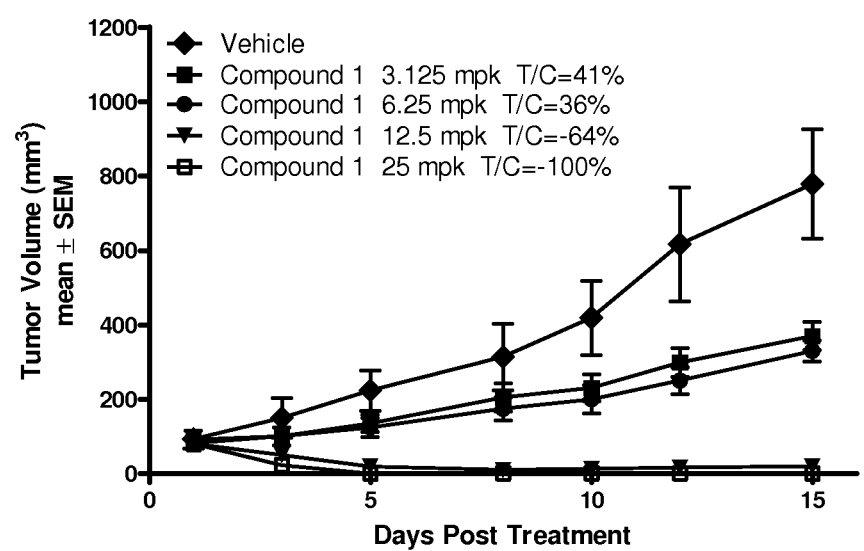
FIG. 1 shows the anti-tumor activity of a compound of Formula I in mouse NCI-H2228 NSCLC model when dosed once a day.
Figure 2:
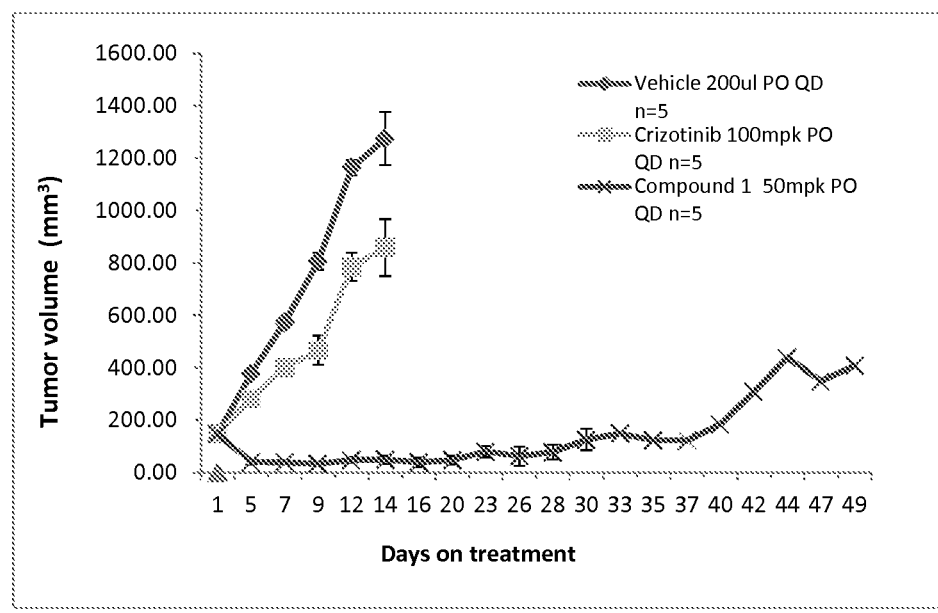
FIG. 2 and FIG. 3 show anti-tumor growth activity of a compound of Formula I in crizotinib resistant NCI-H2228 tumors.
Figure 3:
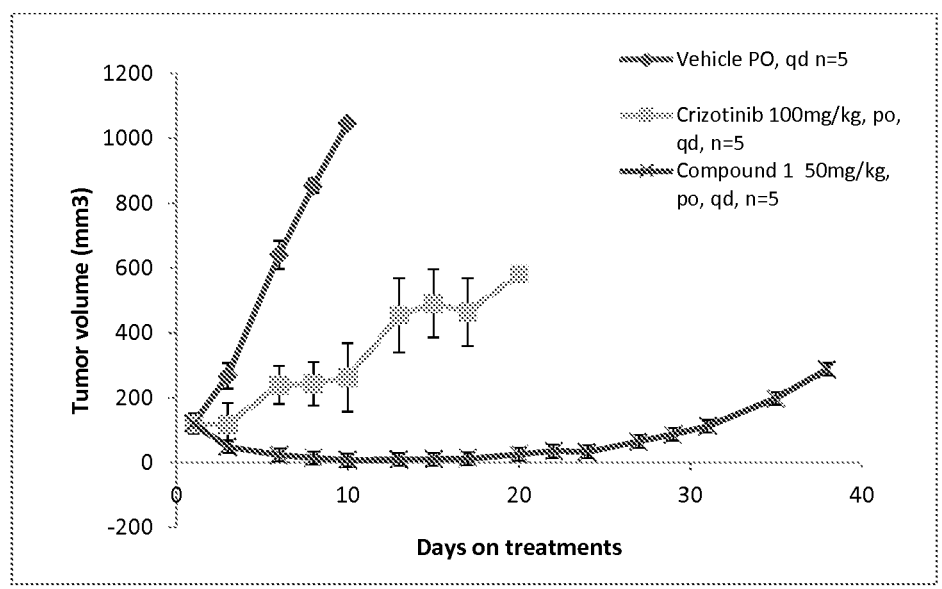

WO 2008/07368A1 describes the preparation of compounds of Formula I. As shown in FIG. 1, a compound of Formula I caused complete tumor regression (T/C=100%) in mouse NCI-H2228 NSCLC model when dosed orally at 25 mg/kg once a day for 2 weeks. As shown in FIG. 2 and FIG. 3, a compound of Formula I showed significant anti-tumor growth activity in crizotinib resistant NCI-H2228. Compound I is studied in clinical trials in both crizotinib-relapsed and crizotinib-naive patients.

In general, a compound of Formula I will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

Example 1

Anti-Tumor Activity in Mouse NCI-H2228 NSCLC Model

In Vitro Cell Growth and Proliferation.

NCI-H2228 cells were obtained from the American Type Culture Collection (ATCC) (Manassa, USA) and modified by viral infection to stably express luciferase. For cell growth and proliferation assays, 2250 cells in 50 µL of RPMI media (Gibco, Carlsbad, Calif.) containing 10% fetal bovine serum (FBS) (Gibco, Carlsbad, Calif.) were plated into solid bottom, white 384-well plates (Corning, Acton, Mass.) using µ-Fill instrumentation (Bio-Tek). Plates were incubated 1 hour in a 37° C. tissue culture incubator prior to the addition of compound using MiniTrak instrumentation (Perkin-Elmer). 50 nL of a 1:3 dilution plate of compounds was added to the assay plates, resulting in final concentrations of 10000, 3333, 1111, 370, 123, 41, 14, 4.6, 1.5, 0.5 and 0.17 nM. After compound addition, plates were incubated for 3 days at 37° C. in a tissue culture incubator. At day 3, plates were assayed for cell growth and proliferation by means of measuring luciferase activity in each individual well. In detail, 25 µL of BRIGHT-GLO® (Promega, Madison, Wis.) or BRIT-ELITE™ (PerkinElmer, Waltham, Mass.) was added to each well. After 10 minutes of incubation at room temperature, plates were read using either an Analyst-GT or an Envision plate reader (Molecular Devices, Sunnyvale, Calif.). The $IC_{50}$ was interpolated as the concentration of compound needed to reduce cell growth and proliferation to 50% of a DMSO control.

Subcutaneous Xenograft Tumor Model Derived from NCI-H2228 Cells.

The day of implantation, NCI-H2228 cells were harvested with 0.05% Trypsin/EDTA and resuspended in a mixture of RPMI 1640 serum-free medium and matrigel (BD Biosciences #354234, La Jolla, Calif.) at a ratio of 1:1. Five million cells were subcutaneously implanted into the right hind flank of SCID beige mouse. When the tumor size reached a volume of 300-400 mm3, the tumors were harvested and were cut into smaller pieces of 1-2 mm3 in culture medium for passage implanting subcutaneously. After the tumors were consecutively passaged three times in SCID beige mice, the tumors were considered as stock tumors for study implantation. The tumor pieces were kept in a mixture of RPMI1640 serum-free medium and matrigel at a ratio of 1:1 on wet ice for implanting in SCID beige mice. Implantation in nude mice: 2-3 pieces of the tumor with matrigel mixture were subcutaneously implanted into the right flank of the mice. After implantation, the tumors were callipered 3 times per week once tumors became palpable.

SCID beige mice bearing the H2228 tumors were randomized into 5 groups (n=4 mice per group) with an average tumor volume of 85±35 mm3. The test compound was administered by oral gavage. Its exposure in the tumor bearing female SCID beige mice was evaluated on day 14. Tumor growth was calculated by % T/C as follows: % T/C=(ΔT/ΔC)×100, where ΔT>0; or % T/C=(ΔT/ΔTI)×100, where ΔT<0. Changes in tumor volume (Δ volumes) for each treated (T) and control (C) group were calculated for each day tumors were measured by subtracting the median tumor volume on the day of first treatment (staging day) from the median tumor volume on the specified observation day.

A shown in Table 1, compounds of Formula I inhibit the in vitro growth and proliferation of human cell line NCI-H2228 with EML4-ALK derived from NSCLC.

TABLE 1

| | $IC_{50}$ (nm) |
|---|---|
| (5-chloro-N2-(2-isopropoxy-5-methyl-4-(piperidin-4-yl)phenyl)-N4-[2-(propane-2-sulfonyl)-phenyl]-pyrimidine-2,4-diamine) (Compound 1) | 11 nm |
| 6-{5-Chloro-4-[2-(propane-2-sulfonyl)-phenylamino]-pyrimidin-2-ylamino}-5-isopropoxy-2-(1-methyl-piperidin-4-yl)-2,3-dihydro-isoindol-1-one (Compound 6) | 16 nm |

When compound 1 was tested in a mouse xenograft model by subcutaneously implanting NCI-H2228 fragment tumor tissues. As shown in FIG. 1, compound 1 caused complete tumor regression when dosed orally at 25 mg/kg once a day for 2 weeks. The compound was well tolerated and animal body weight loss was not observed.

Example 2

Anti-Tumor Activity in Crizotinib Resistant Tumors

The mouse xenograft tumors derived from NCI-H2228 were treated with crizotinib continuously at 50 mg/kg for 9 days, then 75 mg/kg for 9 days and then 100 mg/kg for 33 days. Alternatively, after xenograft tumors derived from NCI-H2228 were treated with crizotinib for 14 days at 100 mg/kg, the treatment with crizotinib was stopped for a few days until tumors re-grew. Once tumors re-grew, animals were treated with crizotinib at 100 mg/kg until tumors became resistant to crizotinib treatment. Tumors from individual animal were harvested when they became resistant to crizotinib. A few such resistant tumors were randomly selected for further studies as described below. Each resistant tumor were cut into small pieces at harvest and implanted into 5 animals; when tumor size was big enough in the 5 animals, the tumors were harvested and then implanted into 25 animals for compound testing. A piece of harvested tumors was also used for RNA extraction and subsequently sequencing of EML4-ALK transcript.

As shown in FIG. 2, (5-chloro-N2-(2-isopropoxy-5-methyl-4-(piperidin-4-yl)phenyl)-N4-[2-(propane-2-sulfonyl)-phenyl]-pyrimidine-2,4-diamine) (Compound 1) showed significant anti-tumor growth activity in crizotinib resistant NCI-H2228. In other crizotinib resistant NCI-H2228 tumors, Compound 1 showed better activity than crizotinib at 100 mg/kg (FIG. 3). Based on 4-wk GLP toxicology studies, the exposure of Compound 1 associated with 50 mg/kg in mouse is predicted to be below the exposure at the MTD in humans.

It is understood that the examples and embodiments described herein are for illustrative purposes only and that various modifications or changes in light thereof will be suggested to persons skilled in the art and are to be included within the range and purview of this application and scope of the appended claims. All publications, patents, and patent applications cited herein are hereby incorporated by reference for all purposes.

The invention claimed is:

1. A method for treating EML4-ALK$^+$ mediated non-small cell lung cancer that is optionally resistant to crizotinib, comprising administering to a cell or subject a compound of Formula (I)

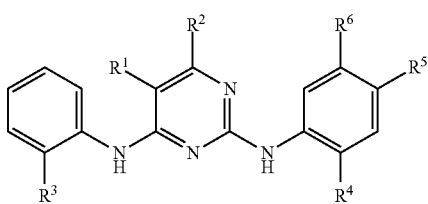

(I)

or a pharmaceutically acceptable salt thereof;
wherein R$^1$ is halo;
R$^2$ is H; or
wherein R$^1$ and R$^2$ together with the carbon atoms to which they are attached form a 5-6 membered heteroaryl comprising 1-2 heteroatoms selected from N, O and S;
R$^3$ is SO$_2$R$^7$ wherein R$^7$ is C$_{1-6}$ alkyl;
R$^4$ is C$_{1-6}$ alkoxy;
R$^5$ is piperidinyl optionally substituted with C$_{1-6}$ alkyl;
R$^6$ is C$_{1-6}$ alkyl; or
R$^5$ and R$^6$ together with the carbon atoms to which they are attached form a 5-6 membered heterocyclic ring comprising having 1-2 heteroatoms selected from N, O and S.

2. The method according to claim 1, wherein the EML4-ALK$^+$ mediated non-small cell lung cancer is resistant to crizotinib.

3. The method of claim 1, wherein R$^1$ in Formula (I) is chloro.

4. The method of claim 1, wherein R$^4$ in Formula (I) is isopropoxy.

5. The method of claim 1, wherein R$^5$ and R$^6$ together with the carbon atoms to which they are attached form —CH$_2$—NR$^8$—C(O)—, wherein R$^8$ is hydrogen or piperidinyl, optionally substituted with C$_{1-6}$ alkyl.

6. The method of claim 1, wherein said compound of Formula (I) is selected from the group:
  5-chloro-N2-(2-isopropoxy-5-methyl-4-(piperidin-4-yl)phenyl)-N4-[2-(propane-2-sulfonyl)-phenyl]-pyrimidine-2,4-diamine;
  5-chloro-N2-(2-isopropoxy-5-methyl-4-(piperidin-2-yl)phenyl)-N4-(2-(isopropylsulfonyl)phenyl)pyrimidine-2,4-diamine;
  (S)-5-chloro-N2-(2-isopropoxy-5-methyl-4-(piperidin-2-yl)phenyl)-N4-(2-(isopropylsulfonyl)phenyl)pyrimidine-2,4-diamine;
  (R)-5-chloro-N2-(2-isopropoxy-5-methyl-4-(piperidin-2-yl)phenyl)-N4-(2-(isopropylsulfonyl)phenyl)pyrimidine-2,4-diamine;
  5-chloro-N2-(2-isopropoxy-5-methyl-4-(piperidin-3-yl)phenyl)-N4-(2-(isopropylsulfonyl)phenyl)pyrimidine-2,4-diamine; and
  6-{5-Chloro-4-[2-(propane-2-sulfonyl)-phenylamino]-pyrimidin-2-ylamino}-5-isopropoxy-2-(1-methyl-piperidin-4-yl)-2,3-dihydro-isoindol-1-one;
or a pharmaceutically acceptable salt thereof.

7. The method of claim 6, wherein said compound is 5-chloro-N2-(2-isopropoxy-5-methyl-4-(piperidin-4-yl)phenyl)-N4-[2-(propane-2-sulfonyl)-phenyl]-pyrimidine-2,4-diamine.

8. The method of claim 6, wherein said compound is 6-{5-Chloro-4-[2-(propane-2-sulfonyl)-phenylamino]-pyrimidin-2-ylamino}-5-isopropoxy-2-(1-methyl-piperidin-4-yl)-2,3-dihydro-isoindol-1-one.

9. The method of claim 1, wherein said subject is a human or animal subject.

* * * * *